US009789070B2

(12) United States Patent
Carullo et al.

(10) Patent No.: US 9,789,070 B2
(45) Date of Patent: Oct. 17, 2017

(54) SHEET PACKS FOR TREATING FACIAL OR BODY SURFACES

(71) Applicant: ELC Management LLC, Melville, NY (US)

(72) Inventors: Anne Carullo, New York, NY (US); Jennifer Palmer Quintano, New York, NY (US); Joyce Kassouf, New York, NY (US); Nadine Pernodet, Huntington Station, NY (US); Donald Collins, Plainview, NY (US); Dawn Layman, Ridge, NY (US); Allan Hafkin, Plainview, NY (US); Osvaldo Fontanet, Emerson, NJ (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 14/810,977

(22) Filed: Jul. 28, 2015

(65) Prior Publication Data
US 2017/0027878 A1    Feb. 2, 2017

(51) Int. Cl.
A61K 9/70    (2006.01)
A61K 36/28    (2006.01)

(52) U.S. Cl.
CPC ............... A61K 9/70 (2013.01); A61K 36/28 (2013.01)

(58) Field of Classification Search
CPC .. A61K 2300/00; A61K 31/045; A61K 31/35; A61K 31/365; A61K 35/74; A61K 36/31; A61K 38/06; A61K 38/07; A61K 38/08; A61K 38/10; A61K 38/43; A61K 8/37; A61K 8/66; A61K 2800/10; A61K 2800/522
See application file for complete search history.

(56) References Cited

U.S. PATENT DOCUMENTS

| | | | |
|---|---|---|---|
| 4,559,047 A | 12/1985 | Kapralis | |
| 5,077,211 A | 12/1991 | Yarosh | |
| 5,190,762 A | 3/1993 | Yarosh | |
| 5,272,079 A | 12/1993 | Yarosh | |
| 5,296,231 A | 3/1994 | Yarosh | |
| 6,221,382 B1 | 4/2001 | Ishida | |
| 7,510,734 B2 | 3/2009 | Sullivan | |
| 2008/0051860 A1 | 2/2008 | Wyk | |
| 2008/0075760 A1 | 3/2008 | Suzuki | |
| 2009/0197939 A1* | 8/2009 | Walke | A61K 8/33 514/450 |
| 2010/0028317 A1* | 2/2010 | Maes | A61K 8/347 424/94.1 |
| 2010/0228204 A1* | 9/2010 | Beatty | A45D 44/002 604/303 |
| 2011/0081391 A1 | 4/2011 | Kawanaka | |
| 2011/0243983 A1 | 10/2011 | Paufique | |
| 2013/0228044 A1 | 9/2013 | O'Kane | |
| 2014/0045766 A1 | 2/2014 | Dal Farra | |
| 2014/0193391 A1* | 7/2014 | Pernodet | A61K 8/66 424/94.61 |
| 2014/0352031 A1 | 12/2014 | Choi | |
| 2015/0071895 A1 | 3/2015 | Pernodet | |
| 2015/0190336 A1 | 7/2015 | Gozu | |

FOREIGN PATENT DOCUMENTS

| | | |
|---|---|---|
| CA | 385753 | 12/1939 |
| CN | 2531785 | 1/2003 |
| JP | 8191718 | 7/1996 |
| JP | 2005281232 | 10/2005 |
| JP | 2014147463 | 8/2014 |
| KR | 10-1999-0029891 | 4/1999 |
| KR | 20070016039 B1 | 2/2007 |

OTHER PUBLICATIONS http://www.gnpd.com; Mintel; Parfums Christian Dior Satin Brightening Mask; Dior Prestige White Collection; Skincare; Face/Neck Care; UK; Record ID 3049547; Mar. 2015.
http://www.gnpd.com; Mintel; Record ID: 1336861; FANCL White Clear Mask; Skincare; Face/Neck Care; Japan; Mar. 2010.
http://www.gnpd.com; Mintel; Record ID: 2214213; L'Occitane Concentrated 3D Mask; L'Occitane en Provence Immortelle Brightening; Skincare; Face/Neck Care; Japan; Sep. 2013.
http://www.gnpd.com; Mintel; Record ID: 2969931; Pola Limited Box; Pola B.A. Grandluxe; Skincare; Sets; Japan; Dec. 2014.
Luber, Adam J., et al.; Therapeutic Implications of the Circadian Clock on Skin Function; Journal of Drugs in Dermatology; vol. 13, Issue 2; pp. 130-134; Feb. 2014.
PCT International Search Report; International Application No. PCT/US2016/042259; Completion Date: Oct. 21, 2016; dated Oct. 21, 2015.
PCT Written Opinion of the International Searching Authority; International Application No. PCT/US2016/042259; Completion Date: Oct. 21, 2016; dated Oct. 21, 2016.
http://www.gnpd.com; Concentrated 3D Mask; Record ID: 2214213; Company: L'Occitane; Category: Skincare; Sub-Category: Face/Neck Care; Country: Japan; Sep. 2013.
http://www.gnpd.com; Limited Box; Record ID: 2969931; Company: Pola; Category: Skincare; Sub-Category: Sets; Country: Japan; Dec. 2014.
http://www.gnpd.com; Satin Brightening Mask; Record ID: 3049547; Company: Parfums Christian Dior; Brand: Dior Prestige White Collection; Category: Skincare; Sub-Category: Face/Neck Care; Country: UK; Mar. 2015.

(Continued)

Primary Examiner — Audrea Buckley
(74) Attorney, Agent, or Firm — Julie Blackburn

(57) ABSTRACT

A sheet pack comprising an absorbent layer impregnated with a treatment composition containing at least one ingredient that when topically applied to skin stimulates a gene that is variably expressed over a 24 hour period in native untreated skin cells; the sheet pack contained in a package with user instructions to topically apply the sheet pack to the skin at a time when the gene that is stimulated by the ingredient is being maximally expressed in native untreated skin cells; and methods for treating skin and methods for making a sheet pack.

20 Claims, 7 Drawing Sheets

(56) References Cited

OTHER PUBLICATIONS http://www.gnpd.com; White Clear Mask; Record ID: 1336861; Company: Fancl Brand: Fancl; Category: Skincare; Sub-Category: Face/Neck Care; Country: Japan; Mar. 2010.
Luber, Adam, et al.; Therapeutic Implications of the Circadian Clock on Skin Function; Journal of Drugs in Dermatology; vol. 13, Issue 2; Feb. 2014; pp. 130-134.

* cited by examiner

CON = control, untreated cells
CON clx = cells treated with Tripeptide-32
O3 = cells treated with ozone
O3 clx = cells treated with ozone and Tripeptide-32

US 9,789,070 B2

SHEET PACKS FOR TREATING FACIAL OR BODY SURFACES

The invention is in the field of sheet packs impregnated with treatment compositions for treatment of facial or body surfaces to provide treatment benefits.

BACKGROUND OF THE INVENTION

The term "sheet pack" originally referred to a procedure where a bed sheet soaked with water was wrapped around a person's body. While the body gradually warmed the sheet the supposedly agitated person was comforted by the warmth and cocoon of surrounding fabric.

Today the term has a broader meaning, and in the beauty industry refers to various sizes and shapes of fabric impregnated with skin treatment compositions for temporary application to skin to provide immediate benefits. Interestingly enough, the comfort aspect of the original sheet packs remains, since today's products are typically used during quiet and restful times of the day or at night. In most cases, today's sheet packs are for facial treatment. They are applied to the face and removed after a short period of time which may range from 1 to 30 minutes. Thereafter the face can either be cleansed or, if appropriate, any treatment composition remaining on the skin is rubbed into the skin. These sheet packs are particularly popular with Asian consumers and sometimes contain active ingredients in larger concentrations than what is found in the creams and lotions typically used as part of the day to day beauty routine.

However, most sheet packs today are formulated with a "kitchen sink" approach and contain many different active ingredients that are touted to have a variety of benefits. There is a failure to appreciate the difference between a treatment benefit and the timing of that treatment benefit in order to maximize efficacy. For example, it is known that in native skin cells, expression of different genes is variable over a 24 hour cycle. This is also referred to as circadian rhythms. Skin care products will sometimes contain active ingredients that are said to stimulate or inhibit expression of certain genes to ultimately cause improvement in undesirable skin conditions such as aging, hyper-pigmentation, moisturization, and so on. However, important in maximizing the effectiveness of any treatment composition or the active ingredients therein is timing. In particular, applying the treatment composition to the treatment surface at a time when the treatment surface is optimized to receive it ensures that the treatment itself is maximally effective.

Accordingly, it is an object of the invention to provide a sheet pack with optimized efficacy due to the presence of the sheet pack constituents and a treatment composition that contains at least one active that stimulates expression of a specific gene in skin cells that is normally variably expressed in untreated native skin cells and optionally at least one second skin treatment active ingredient that provides a benefit; and where the sheet pack is applied to the treatment surface (e.g. skin) at a time when the ingredient in the treatment composition that stimulates expression of the specific gene is being maximally expressed in the majority of native untreated skin cells so that the treatment benefit of the ingredient is optimized.

DEFINITIONS

All percentages stated herein are percentages by weight unless otherwise indicated.

"BMAL" means the aryl hydrocarbon receptor nuclear translocater-like protein 1 which is coded for by the ARNTL or BMAL gene and affects circadian rhythms.

"CLOCK" means Circadian Locomotor Output Cycles Kaput gene, present in skin cells, that codes for proteins (CLK) that impact circadian rhythms, which are generally affected by light and darkness.

"CRY" means cryptochrome circadian genes which codes for a protein that affects circadian rhythms, both versions 1 and 2.

"PER" means the Period gene (1, 2, or 3) that encodes the period circadian protein homolog protein in humans. Per1 in particular is important to the maintenance of circadian rhythms and ebbs and flows over a 24 hour cycle. Cellular Per1 gene expression is most active at night, ebbs during daylight hours, and increases again during periods of darkness.

"Sheet pack" means a thin sheet of material that may be sized and shaped to fit a facial or body surface and is designed to be applied for a temporary period of time to provide some cosmetic or therapeutic improvement to the keratin surface such as skin in the area where the pack was applied.

"Sheet mask" means a sheet pack which has been sized and shaped for placement on the face, and may contain cut out portions for the eyes, nose, or mouth.

"Benefit" means the benefit that a product, when used as directed, is designed to provide. The product manufacturer's advertised benefits (or claims) are generally what prompts the consumer to buy the product to begin with. Benefits typically fall into categories such as anti-aging treatment (treating lines and wrinkles), anti-aging optics (blurring the appearance of skin imperfections), moisturization (moisturizing dry skin), anti-inflammation (treating irritated or inflamed skin to reduce redness, pain, or heat), SPF (blocking UVA and/or UVB rays), anti-acne (treating acne lesions, excessive skin oiliness), skin whitening (whitening skin or improving hyperpigmented spots), and so on.

SUMMARY OF THE INVENTION

Figure 1:
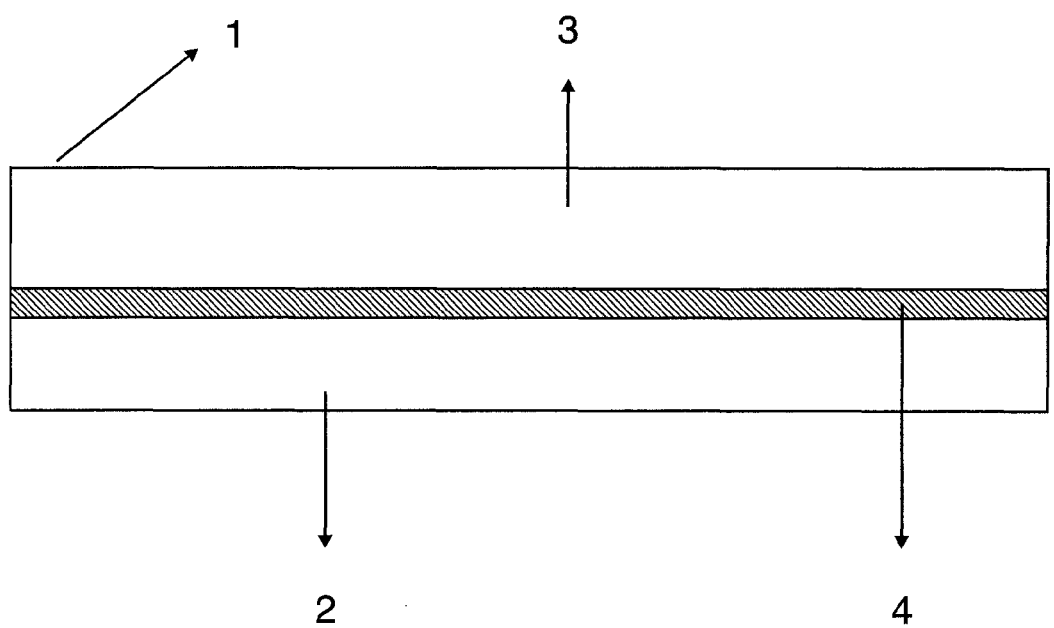
FIG. 1 depicts an embodiment of the invention where the sheet pack is in laminate form and the absorbent layer is bonded to the impermeable layer with the bonding agent.

The invention is directed to a sheet pack comprising an absorbent layer impregnated with a treatment composition containing at least one ingredient that when topically applied to skin stimulates a gene that is variably expressed over a 24 hour period in native untreated skin cells and optionally in combination with at least one benefit agent; the sheet pack contained in a package with user instructions to topically apply the sheet pack to the skin at a select time period within the 24 hour time period when the same gene that is stimulated by the ingredient is being maximally expressed in native untreated skin cells.

The invention is also directed to a method for making a sheet pack comprising the steps of:

(a) identifying a gene that is variably expressed over a 24 hour period in native untreated skin cells, (b) forming a sheet pack comprised of an absorbent layer and, optionally, an impermeable layer bonded to the absorbent layer, (c) impregnating the absorbent layer with a treatment composition containing at least one ingredient that stimulates the gene in (a) above when topically applied to skin;

(d) packaging the sheet pack in a package containing user instructions to apply the sheet pack to the skin a time when the gene in (a) above is being maximally expressed in the majority of native untreated skin cells.

The invention is also directed to a method for treating skin with a sheet pack comprising the steps of:

(a) forming a sheet pack comprised of absorbent layer and optionally bonded thereto an impermeable layer;

(b) impregnating the absorbent layer with a treatment composition containing at least one ingredient that stimulates a gene that is variably expressed over a 24 hour period in native skin cells when topically applied thereto, (c) topically applying the sheet pack to the skin at a time when same gene in (b) above is being maximally expressed in native untreated skin cells.

DETAILED DESCRIPTION

The various components and embodiments of the invention will be described in detail herein.

The Sheet Pack

The invention is directed to a sheet pack comprising an absorbent layer and optionally an impermeable layer bonded to the absorbent layer, where the absorbent layer is impregnated with a treatment composition containing at least a one ingredient that has activity in stimulating a gene that is variably expressed over a 24 hour period in native skin cells. This ingredient may also be a skin treatment active, or it may be desirable to incorporate at least one additional skin treatment active into the composition. The sheet pack is contained in a package with user instructions to topically apply the sheet pack to the skin at a time when the same gene that is stimulated by the ingredient is being maximally expressed in native untreated skin cells.

A. The Impermeable Layer

The sheet pack of the invention is in the form of a laminate and optionally contains at least one impermeable layer. The term "impermeable" means that the layer is generally impermeable to moisture so that evaporation of the active formula from the sheet mask absorbent layer may be substantially reduced or inhibited entirely. The impermeable layer used in the laminate may be made of metallic foil, synthetic polymeric materials, or natural polymeric materials that are capable of existing in the form of a thin film. Particularly preferred is metallic foil.

Metallic Foil

Suitable metallic foil may be a metal alloy containing aluminum, silica, iron, copper, manganese, magnesium or zinc. Preferred is aluminum foil from metal alloys containing 0.1 to 1.0% of a combination of silica andiron, 0.01 to 0.12% copper, 0.001 to 0.06% Manganese, 0.001 to 0.06% Magnesium, 0.001 to 0.06% Zinc, and greater than about 98% aluminum, preferably from about 98 to 100% aluminum. The preferred aluminum foil is in a solid form, silver in color, and has a melting point greater than 650° C., and a specific gravity ranging from 2.5 to 3.0, preferably about 2.7. Most preferred is an aluminum foil having a thickness ranging from 2 to 15 microns, preferably from about 5 to 10 microns, more particularly, about 7 microns. Most preferred is an aluminum foil alloy made by Toyo KK, Osaka Japan.

Synthetic Polymer Sheets

Examples of impermeable layers suitable for preparation of the laminate also includes polyvinylidene chloride, polyethylene, or other homo- or copolymer of ethylenically unsaturated monomers that are operable to form a film in thin sheets having a thickness ranging from 2 to 20 microns. Examples of such impermeable layers suitable for the laminate include polyvinylidene chloride or polyethylene, of the kind often referred to by the trademark "Saran Wrap" as set forth in Canadian Patent No. 385753. Preferred synthetic polymeric impermeable layers have functional characteristics similar to those of the metallic foil including a specific gravity (density) ranging from 2.5 to 3.0, preferably about 2.7.

The impermeable layer provides a barrier that aids in penetration of active ingredients into the skin, reduces evaporation of water and fluids from the mask, and generally improves effectiveness of the treatment.

B. The Absorbent Layer

The absorbent layer used to create the sheet mask is preferably made from nonwoven fabric. Non-woven fabrics refer to those that are neither knitted nor woven. They are typically formed by entangling fibers or filaments mechanically, thermally, or chemically. Nonwoven fabrics suitable for the absorbent layer have various preferred functional properties.

First, the most suitable nonwoven fabrics should have good water or liquid absorption properties. That is, the fabric should be capable of absorbing and retaining liquids. Suitable nonwoven fabrics can be identified by measuring water absorption capability according to the Larose method. In this case, examples of suitable nonwovens may have water absorption readings ranging from about 0.03 to 2.5 ml/gram after 5 seconds per 1 gram. More preferred is where the water absorption capacity ranges from 0.30 to 2.5 ml/gram. If the water absorption capacity is too low (below 0.03 ml/gram) the nonwoven fabric may not be capable of absorbing enough of the treatment composition to treat the desired keratin surface area. For example, in a face mask application, it is desired that the absorbent layer contain from about 15 to 50 ml, more preferably 20-40 ml. Most preferred is a fill of about 24-25 ml. in a face mask with a surface area ranging from 55 to 80 square inches.

In one preferred embodiment the nonwoven fabric has a thickness ranging from 0.1 to 1.0 mm, preferably 0.2 to 0.8 mm, more preferably from 0.5 to 0.7 mm.

Suitable nonwoven fabrics must also have a flexibility that is sufficient to enable the fabric to readily drape onto the treatment surface and remain in place on the treatment skin surface even with slight movements. This property is typically quantified by measuring bending resistance, preferably by the cantilever stiffness method (IST 90.1-86 or ASTM D1388). In one embodiment the nonwoven fabric may have a bending resistance of 1.0 to 2.0 mm·m$^2$/gram.

Another property of suitable nonwoven fabrics that can be used in the invention is quantified by drape resistance. Suitable nonwoven fabrics include those having a drape co-efficient ranging from 1 to 70%, preferably from about 25-70% or 50-68%. The higher the drape co-efficient, the less drapeable the fabric. In preparing sheet packs for treating body surfaces, drape is an important consideration. The sheet pack must be capable of draping on the treatment surface.

In another embodiment, the KES bending rigidity B value of the nonwoven fabric is 0.20 gf/cm$^2$/cm or lower, and provides fabric that is soft and easily bent.

In addition, one preferred embodiment of nonwoven may be characterized by its friction co-efficient, which is one measurement by which a smooth feel can be quantified. The formula for calculating friction co-efficient is:

$$\mu = F/N$$

wherein F is the force required to move an object on the horizontal surface and N is the load normal to the surface. Friction is preferably measured by the friction tester. In one preferred embodiment the co-efficient of friction for the nonwoven fabric is less than 0.45 MIU. Fabrics with measurements of greater than 0.45 MIU may tend to provide a hard feeling to the touch.

Examples of fibers that may be used to prepare the nonwoven fabric of the absorbent material include cellulose, rayon, wool, silk, cellulose acetate, synthetic or semi-synthetic fibers. Fibers may also be composites of natural and synthetic fibers.

Cellulose fibers may be natural or synthetic. When the cellulose fibers are hydrophilic the water absorption and retention properties of the nonwoven fabric are improved. Examples of natural cellulose fibers include wood pulp, pulp from non-wood sources, cotton, cotton lint, etc. Pulp fibers may be from hard or soft wood pulp and from bamboo, straw, tree bark, hemp, jute, and the like. Soft wood pulp is particularly suitable because of its longer fiber lengths which retain integrity during the bonding process used to create nonwoven fabrics, where hard wood pulp, with its shorter fiber length is not optimal. Particularly desirable are non-woven fabrics where the pulp comprises 5 to 90%, preferably 20-80%, more preferably 40-70% of the nonwoven fabric composition.

It may be desirable to include rayon fibers in the nonwoven fabric composition. Rayon, made from regenerated cellulose fibers, will increase strength and water absorption in nonwoven fabrics. The amount of rayon fibers may range from 10-90%, preferably from 20-80%, more preferably from 25-75% of the total nonwoven fabric composition. Combining rayon and cellulose fibers provides a nonwoven fabric with good feel, water absorption, and strength.

It may also be desirable to include synthetic fibers in the nonwoven fabric. Examples of such synthetic fibers include homo- and copolymers of polyamides, polyacrylonitriles, polyolefins, polyesters, or polyvinyl alcohol such as polyethylene terephthalate (PET), polytetramethylene terephthalate (PTT), polypropylene, and the like. If desired the nonwoven may contain from 1-75%, preferably 5 to 50%, more preferably from about 5 to 30% of such synthetic fibers. If the amount of synthetic fibers is too great, e.g. greater than 60-70%, the water absorption of the nonwoven fabric is decreased and the treatment composition is not readily transferred to the treatment surface when the nonwoven fabric is placed thereon. The transfer of the treatment composition impregnated into the absorbent layer can be maximized if the synthetic fibers are somewhat oleophilic. This causes the moisturizing composition to be more readily exuded from the absorbent layer into the skin. In one preferred embodiment the synthetic fibers are PET.

Particularly preferred is where the absorbent layer is a non-woven fabric containing about 25-75% pulp (cotton), 10-50% rayon, and 2-15% polyester, more preferably about 55+/−5% pulp, 35+/−5% rayon, and 10%+/−5% polyester. An example of this non-woven fabric can be purchased from Sansho Shigyo Co. Ltd. In other preferred embodiments the fabric has one or more of the functional parameters mentioned above, specifically, water absorption, drape co-efficient, KES bending rigidity, and friction co-efficient.

C. The Bonding Agent

Lamination of the absorbent layer and the impermeable layer, if desired, is accomplished with a bonding agent. The bonding agent must secure the two layers together in permanent fashion, be compatible with the impermeable and absorbent layers and the treatment composition, and be operable to fuse the layers together with application of pressure and heat. The heat used to effectuate bonding must be low enough to effectively laminate the two layers yet not high enough to cause burning, disintegration, melting, or other disruption of the absorbent layer. In one embodiment the bonding agent has a melting point ranging from 200 to 300° C. and may be operable to effectively fuse the absorbent layer and the impermeable layer at a temperature that is from about 1 to 35% less than its melting temperature. Most preferred is a polymer from ethylenically unsaturated monomer repeat units such as acrylic acid, methacrylic acid or their simple C1-20 alkyl or aromatic esters; or ethylene, propylene, butylene repeat units. Particularly preferred is polyethylene, in particular a low density polyethylene sold by Tosoh Corporation under the trade name Petrothene which has a melting point of 221 to 248° C. and is in a solid form of milky white pellets, with a specific gravity of 915 to 935 kg/m$^3$. Most preferred is where the bonding agent has a melting point ranging from 200 to 300° C. and bonds the impermeable layer to the absorbent layer at a temperature ranging from about 300 to 400° C.

D. Bonding of the Absorbent and Impermeable Layers

In the case where the sheet pack is in laminate form, the absorbent layer and the impermeable layer must be bonded together to form a laminate where the absorbent layer is adhered to the impermeable layer. The bonding is best achieved by placing an extruder with the bonding material between two separate spools of the nonwoven fabric and the metallic foil layer and extruding the bonding material between the two layers with a sufficient amount of pressure and heat to cause the layers to become laminated together, then spooling the laminate onto a separate collecting roller.

The laminate 1 formed by bonding the absorbent layer 2 to the impermeable layer 3 with the bonding agent 4 is depicted in FIG. 1.

Figure 2:
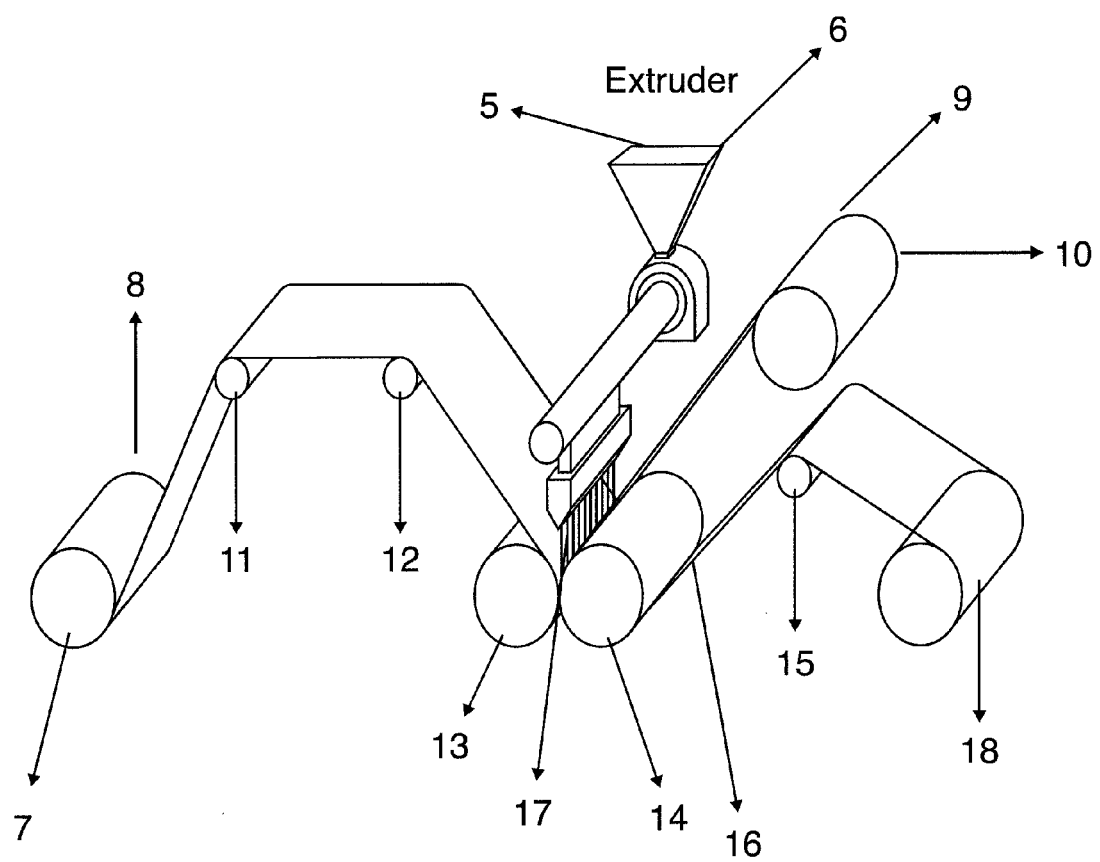
FIG. 2 depicts one type of apparatus that may be used to create the laminate and bond the impermeable layer and absorbent layer with the bonding agent.

A suitable apparatus for performing the lamination is best depicted in FIG. 2. The bonding material 17 is fed into the inlet port 5 of the extruder 6. The nonwoven fabric 7 is on one spool 8 and the impermeable layer in the form of metallic foil 9 placed on a second spool 10. When the apparatus is engaged, the nonwoven fabric 7 is fed over guiding spools 11 and 12 that revolve and feed the nonwoven film layer across over the two revolving spools 11 and 12 and onto a larger revolving spool 13 that abuts another larger revolving spool 14 such that when spool 13 revolves in a clockwise direction the spool 14 revolves in a counter-clockwise direction and the absorbent layer 7 and the metallic foil layer 9 are fed between spools 13 and 14 and the bonding material 17 is fed between the two layers with pressure and heat to cause the foil layer 9 and the nonwoven fabric 7 to become bonded together.

Second spool 10, similarly revolves to feed metallic foil layer 9 into spools 13 and 14. The metallic foil layer 9 is fed from second spool 10 to larger spool 14 and pressure and heat applied as the bonding material 17 is fed between the two layers to bond them together and form the laminate 1. The laminate formed when the bonded layers are fed out of spools 13 and 14 is fed along smaller spool 15 and stored on receiving spool 18 for later cutting into the desired sizes and shapes. The treatment composition (more fully described below) can be impregnated into the absorbent layer either before or after the laminate is cut into the desired shape for the treatment surface.

More specifically, it is preferred that the temperature at which the bonding of the layers mentioned above takes place ranges from 300 to 400° C., preferably from 325 to 360° C., most preferably from 330 to 335° C. The most optimal pressure for the bonding ranges from 2.5 to 4.0 Pascal, more preferably from 2.75 to 3.25 Pascal, most preferably from about 2.8 to 3.2 Pascal or in particular 3.0 Pascal.

The laminate formed from the nonwoven fabric layer, the bonding agent layer, and the impermeable layer preferably has a thickness ranging from 0.2 to 1.5 mm, preferably from about 0.2 to 1.0 mm, most preferably from 0.3 to 0.8 mm. This thickness provides a sheet pack that has optimal strength and resiliency.

E. Impregnating Treatment Composition into the Absorbent Layer

The treatment composition, more specifically described herein, is preferably impregnated into the absorbent layer after the lamination process either prior to cutting the laminated roll into the desired shapes and sizes desired for the treatment surface or after cutting the customized shapes. It is most preferred that the impregnation of the treatment composition into the absorbent layer occurs after the laminate has been cut into the desired size and shape. In one embodiment of the invention the treatment composition may be contained in a separate container and applied to the mask by the consumer. In this case the sheet mask and a container filled with the treatment composition are sold in the form of a kit purchased by the consumer. Immediately prior to use the consumer applies the treatment composition to the absorbent layer of the mask for treatment of the skin.

F. The Sheet Mask Shapes

The laminate is then cut into the desired shapes depending on the surface to be treated. For example, facial treatment sheet packs can be cut in a variety of configurations suitable for application to the face. These shapes include one piece masks that cover the entire facial surface, or various smaller pieces that can be placed in desired strategic areas such as under the eyes, around the mouth, or on dry areas of skin.

Figure 3:
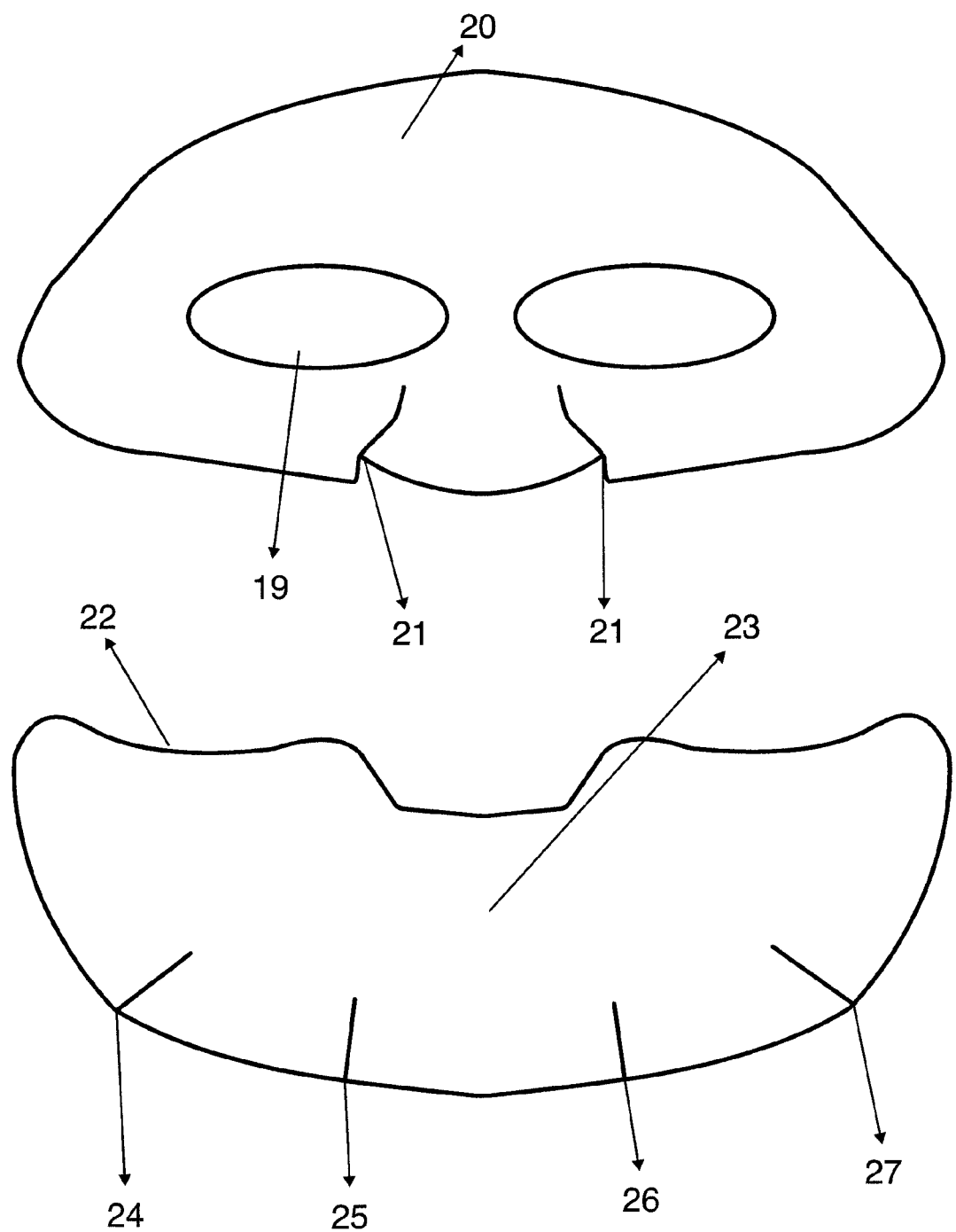
FIG. 3 depicts a type of sheet pack in the form of a facial treatment mask in two pieces—a piece designed for treatment of the top half of the face and a second piece for application to the bottom half of the face.

Most preferred is a face mask in two sections as depicted in FIG. 3, where a top portion covers the area between the forehead and the nose and the bottom portion covers the around beneath the nose and to the check or neck. The two piece mask of FIG. 3 has two eye slits 19 that are large enough so that the upper section of the mask 20 fits on the top part of the face but does not occlude the eyes. Slits on either side of the nose 21 enable the mask portion to treat the bridge area of the nose. The mask section for treatment of the lower half of the face 22 has an open section 23 just large enough to surround the lips. Various slits 24, 25, 26, and 27 are preferably embedded in lower face mask 22 to permit easier draping around the chin.

The Sheet Pack Container and User Instructions

Figure 4:
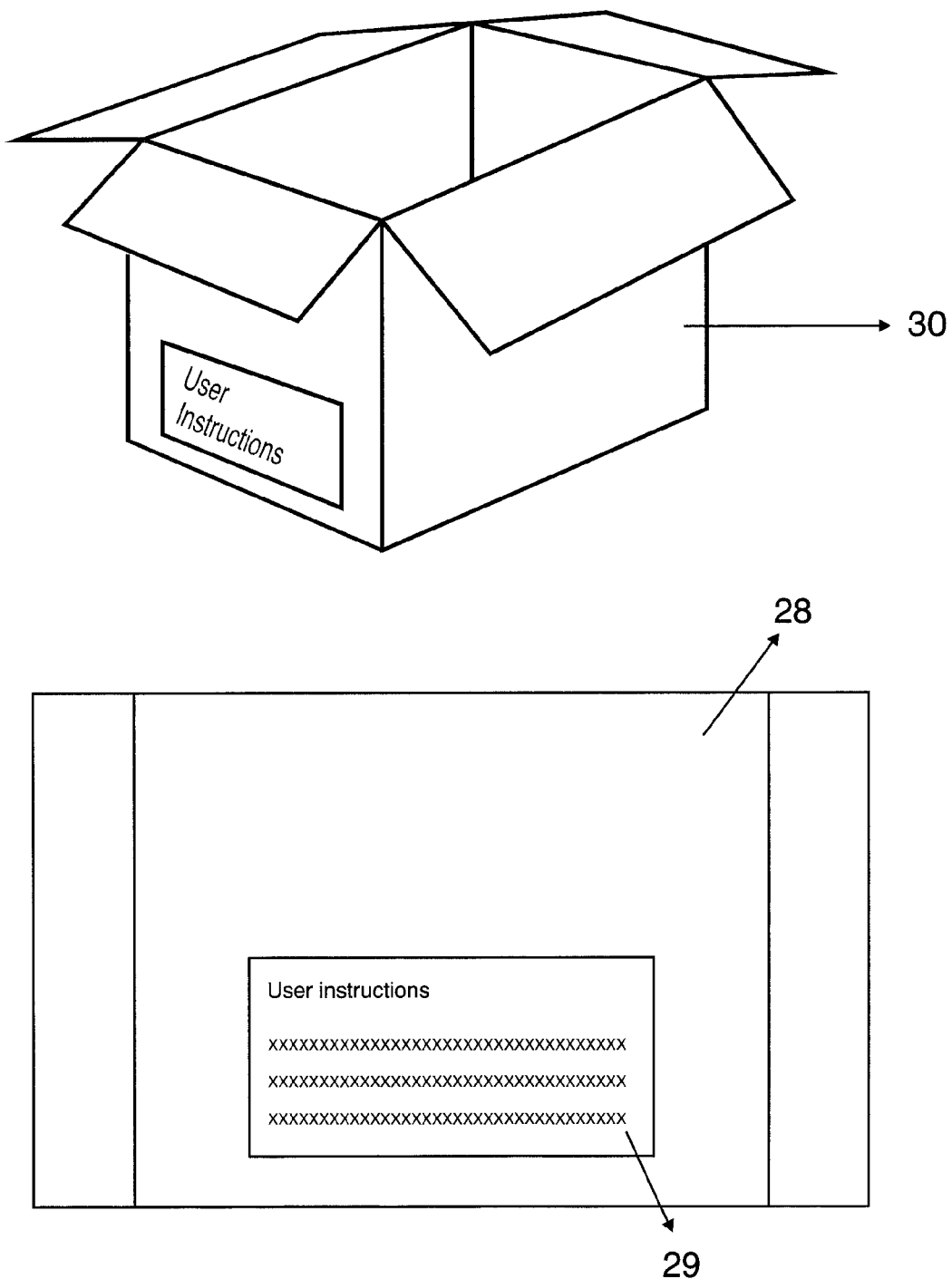
FIG. 4 depicts various types of packages and pouches in which the sheet pack is contained and user instructions on the optimum time to apply the sheet pack to the skin.

The sheet pack that is cut to fit the desired keratin surface is the contained in a package which is preferably a hermetic pouch or envelope 28 as depicted in FIG. 4. One type of package is depicted in FIG. 4. The envelope for holding the sheet pack may be of a size and shape to ensure that the sheet mask can remain unfolded. Alternatively, it may be more desirable to fold the sheet pack in halves or fourths and store in an envelope 28 that is smaller in size. The user instructions can be placed directly on the envelope 29, or alternatively, on a secondary package 30 in which one or more of the envelopes 28 are placed. The secondary package may a box 30 for holding one or more individual sheet packs contained in storage envelopes 28. The user instructions instruct the user to apply the sheet pack at a time when the same gene activated by the ingredient in the treatment composition is being maximally expressed in native skin cells.

The Treatment Composition

The treatment composition used in the sheet pack of the invention is preferably in liquid form. It may be an emulsion (either oil in water or water in oil) or in a solution or dispersion form. A particularly preferred form is referred to as a serum, which is generally a mixture of water, humectants, and other ingredients and contains very little to no oil phase. A suitable treatment composition for impregnating into the sheet pack may have a viscosity ranging from 2 to 1000, preferably from about 2 to 200, more preferably from about 5-50 cps at 25° C. and a specific gravity ranging from 1.000 to 1.010, more preferably about 1.000 to 1.008, most preferably about 1.005. Maintaining the treatment composition within the viscosity and specific gravity ranges ensures that it will properly impregnate the absorbent layer and be sufficiently liquid to permeate the layer but not so viscous to create difficulty in permeating the layer.

If the treatment composition is in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

Particularly suitable is a treatment composition that contains at least one active ingredient that has activity in stimulating a gene that is variably expressed over a 24 hour period in native skin cells and optionally at least one skin treatment active that provides a benefit. The composition may contain other ingredients that contribute to providing a stable and commercially acceptable formula.

The active ingredient that simulates the gene variably expressed over a 24 hour period may act by synchronizing the treated cells so that their biological (circadian) pathways are all operating synchronously, particularly when the sheet pack is applied consistently over time. Alternatively, this active ingredient may also act by supplementing the depleted state of native skin biological proteins that stimulate the variably expressed gene; a condition often seen at the end of the day. The ingredient with its activity in stimulating the variably expressed gene will maximize the effectiveness of one or more benefit actives so that their effects on the treatment surface are optimized.

A. The Active that Stimulates the Variably Expressed Gene

Examples of variably expressed genes in skin cells include period homolog genes (PER1, 2, and 3), Circadian Locomotor Output Cycles Kaput (CLOCK), Chryptochrome Circadian Clock 1 or 1 (CRY1, 2), and Brain and Muscle Arylhydrocarbon Receptor Nuclear Translocator (BMAL), etc. These genes are generally referred to as circadian genes because they are variably expressed in skin cells over a 24 hour period, with the peak expression usually occurring in the evening to night time hours.

Active ingredients that stimulate expression of these genes in skin cells (e.g. keratinocytes, fibroblasts, adipocytes, etc.) may stimulate one or more of PER, CLOCK, CRY, or BMAL genes and include, but are not limited to those set forth herein. The ingredient that stimulates expression of the variably expressed gene may be present in the treatment composition in amounts ranging from 0.00001 to 8%, preferably from about 0.0005 to 5%, more preferably from about 0.001 to 3%.

*Echinacea*—Cichoric Acid

*Echinacea* extract, or the active component derived therefrom, cichoric acid has been shown to be a suitable activator of PER and PER1 in particular. The cichoric acid component may be synthetic or naturally derived. Synthetic cichoric acid may be purchased from a number of commercial manufacturers including Sigma Aldrich. Cichoric acid may also be extracted from botanical sources that are known to contain cichoric acid such as *Echinacea, Cichorium, Taraxacum, Ocimum, Melissa*, or from algae or sea grasses. More specifically, botanical extracts such as *Echinacea purpurea, Cichorium intybus, Taraxacum officinale, Ocimum basilicum*, or *Melissa officinalis* are excellent sources. The term "cichoric acid" when used herein also includes any isomers thereof that are operable to increase PER1 gene expression in skin cells.

Most preferred is a botanical extract from *Echinacea purpurea* sold by Symrise under the brand name Symfinity™ 1298 which is an extract of *Echinacea purpurea* which is standardized during the extraction process to contain about 3% by weight of the total extract composition of cichoric acid. *Echinacea* extracts from different sources will vary in cichoric acid content, and as such will yield variable results in induction of per1 gene expression. For example, we have observed that another component commonly found in extracts of *Echinacea*, specifically caftaric acid, does not increase PER1 gene expression in skin cells. Moreover, each species of *Echinacea* will differ in content of phenolic and cichoric acids. Ethanolic extract of the roots of *Echinacea purpura* will provide more cichoric acid than ethanolic extracts of *Echineacea angustifolia* or *Echinacea pallida*. The content of active ingredients in any extract is also very dependent on the method of extraction. For example, it is known that in many cases enzymatic browning during the extraction process will reduce the phenolic acid content of the resulting extract. The *Echinacea* extracts with optimal cichoric acid content are preferably extracted in ethanol. Alternate extractions may be water only, water and alcohols in admixture, or alcohols alone with the alcohols selected from methanol, ethanol, and those of similar lower carbon chain lengths such as propanol, isopropanol, and so forth.

Peptides

A variety of peptides are suitable CLOCK or PER1 gene activators. One example of such a peptide is disclosed in U.S. Patent Application No. 2014/0045766 which is hereby incorporated by reference in its entirety.

Such peptides have the general formula:

$R_1\text{-}(AA)_n\text{-}X_1\text{-}S\text{-}T\text{-}P\text{-}X_2\text{-}(AA)_p\text{-}R_2$ Where $(AA)_n\text{-}X_1\text{-}S\text{-}T\text{-}P\text{-}X_2\text{-}(AA)_p$ is (SEQ ID No. 1) and:
$X_1$ represents a threonine, a serine, or is equal to zero,
$X_2$ represents an isoleucine, leucine, proline, valine, alanine, glycine, or is equal to zero,
AA represents any amino acid or derivative thereof, and n and p are whole numbers between 0 and 4,
$R_1$ represents the primary amine function of the N-terminal amino acid, either free or substituted by a protective grouping that may be chosen from either an acetyl group, a benzoyl group, a tosyl group, or a benzyloxycarbonyl group,
$R_2$ represents the hydroxyl group of the carboxyl function of the C-terminal amino acid, substituted by a protective grouping that may be chosen from either a $C_1$ to $C_{20}$ alkyl chain or an $NH_2$, NHY, or NYY group with Y representing a $C_1$ to $C_4$ alkyl chain,
wherein the sequence of general formula (I) comprises from about 3 to 13 amino acid residues,
said sequence of general formula (I) possibly containing substitutions of amino acids $X_1$ and $X_2$ with other chemically equivalent amino acids;
wherein the amino acids are:
Alanine (A)
Arginine (R)
Asparagine (N)
Aspartic Acid (D)
Cysteine (C)
Glutamic Acid (E)
Glutamine (Q)
Glycine (G)
Histidine (H)
Isoleucine (I)
Leucine (L)
Lysine (K)
Methionine (M)
Phenylalanine (F)
Proline (P)
Serine (S)
Threonine (T)
Tryptophan (W)
Tyrosine (Y)
Valine (V)

More preferred are peptides of the above formula as follows:

```
S-T-P-NH2
Ser-Thr-Pro-NH2
```

```
                                       (SEQ ID No. 2)
Y-V-S-T-P-Y-N-NH2
Tyr-Val-Ser-Thr-Pro-Tyr-Asn-NH2
```

```
                                       (SEQ ID NO. 3)
NH2-V-S-T-P-E-NH2
NH2-Val-Ser-Thr-Pro-Glu-NH2
```

```
                                       (SEQ ID No. 4)
NH2-L-H-S-T-P-P-NH2
NH2-Leu-His-Ser-Thr-Pro-Pro-NH2
```

```
                                       (SEQ ID No. 5)
CH3NH-R-H-S-T-P-E-NH2
CH3-NH-Arg-His-Ser-Thr-Pro-Glu-NH2
```

```
                                       (SEQ ID No. 6)
CH3NH-H-S-T-P-E-CH3NH
CH3-NH-His-Ser-Thr-Pro-Glu-CH3-NH
```

More preferred is the S-T-P-NH$_2$ peptide, or mixtures thereof.

Most preferred is a peptide manufactured by ISP-Vincience under the trademark Chronolux® having the INCI name Tripeptide-32.

Another suitable peptide is as disclosed in U.S. Patent Application No. 2011/0269694, hereby incorporated by reference in its entirety and has the formula:

(SEQ ID No. 7) $R_1$-$X_1$-$X_2$-Ser-Pro-Leu-Gln-$X_3$-$X_4$-$R_2$ wherein:
$X_1$ is cysteine, a methionine or is equal to zero,
$X_2$ is serine, threonine, or is equal to zero,
$X_3$ is alanine, glycine, isoleucine, leucine, proline, valine or is equal to zero. $X_4$ is asparagine, glutamine, or is equal to zero.
$R_1$ is the primary amine function of the N-terminal amino. acid, either free or substituted by a protective group which can be selected from an acetyl group, a benzoyl group, a tosyl group or a benzyloxycarbonyl group,
$R_2$ is the hydroxyl group of the carboxyl function of the C-terminal amino.acid, either free or substituted by a protective group which can be selected from a C1-20 alkyl chain or a $NH_2$, NHY or NYY group where Y is a C1-4 alkyl chain, said sequence of general formula (I) being formed of 4 to 8 amino acid residues, said sequence of general formula (I) possibly comprising substitutions of amino acids $X_2$ to $X_4$ with other chemically equivalent amino acids.

More preferred is a peptide wherein the substituents are selected to provide the following:

(SEQ ID No. 8) Ser-Pro-Leu-Gln-$NH_2$.

This peptide may be purchased from ISP-Vinscience under the trademark Chronogen® having the INCI name Tetrapeptide-26.

Also suitable as activators of one or more of PER, CLOCK, BMAL, or CRY, are ingredients that are activators of the cellular autophagy process. In general, the cellular autophagy process comprises four general steps. Step 1 is the initiation of vacuole formation; Step 2 the formation of the initial vacuole or autophagosome which sequesters the cytoplasmic material to be degraded. Step 3 is the maturation of the autophagosome into a degradative vacuole. Step 4 is the actual degradation of the sequestered material.

Ingredients with autophagy activation activity can be identified by their ability to either stimulate or inhibit various cellular metabolic pathways. For example, ingredients that stimulate the expression of MAP-LC3, ATG5-12, protein p53, AMPK, or DRAM genes are suitable autophagy activators. Ingredients that inhibit the expression of mTOR genes are also suitable autophagy activators.

The gene MAP-LC3 codes for microtubule-associated protein 1 light chain 3, a protein that initiates formation of autophagosomes. ATG5-12 also stimulates formation of autophagosomes. mTOR, also known as mammalian target of rapamycin, is also known as the mechanistic target of rapamycin or FK506 binding protein 12-rapamycin associated protein 1 (FRAP1). FRAP1 is encoded by the FRAP gene. Any ingredient that inhibits the expression of mTOR, involved in autophagosome creation, will have autophagy activating properties. Also suitable as autophagy activators are ingredients that stimulate expression of protein p53, AMPK, and/or DRAM (damage remedy autophagy modulator protein) in keratinocytes. Protein p53, also known as a tumor suppressor protein, is encoded by the p53 gene. AMPK means AMP activated protein kinase and DRAM, damage related autophagy modulator. Both are known to stimulate autophagy activation in keratinocytes.

Thus any ingredient that has the above mentioned effects on the genes may be suitable autophagy activators and activators of PER, BMAL, CLOCK, or CRY. During the autophagocytic process cellular debris such as oxidized proteins and peroxidized lipids are degraded. Such cellular debris often affects normal metabolic function. Screening of ingredients to determine efficacy by ability to stimulate or inhibit cellular, preferably keratinocyte, genes and/or proteins mentioned above may be done according to methods as set forth in US Patent Publication No. 2011/0243983, incorporated by reference in its entirety, or other methods known in the art.

For example, one general process for identifying ingredients that may be autophagy activators is by first inducing nutritive stress in cultured cells such as keratinocytes. For example, the cells are first cultured in complete culture medium with growth factors, for about 24 hours. The culture medium is then removed and replaced with a non-nutritive culture medium, for example one that does not contain growth factors. The cells are cultured for about 30 minutes to about 25 hours in a state of nutritive stress. Then, the non-nutritive culture medium is removed and replaced with complete culture medium to promote cellular recovery. Thereafter, the cells are evaluated for autophagocytic activity by measuring the expression of one or more of MAP-LC3; ATG5-12; phosphorylated mTOR; phosphorylated p53; DRAM; or phosphorylated AMPK in those cells. Measurement of such expression can take place by immunofluorescence measurements. In addition, the expression can be ascertained by Western Blot analysis of phosphorylated proteins associated with the expressed genes.

Examples of ingredients that are known to exert either the stimulatory or inhibitory effects on the above mentioned genes which, in turn, stimulate autophagy and activate one or more of PER, CLOCK, CRY, or BMAL, are yeast extracts including but not limited to those from the genuses such as *Lithothamnium, Melilot, Citrus, Candida, Lens, Urtica, Carambola, Momordica, Yarrowia, Plumbago*, etc. Further specific examples include *Lithothamniumn calcareum, Melilotus officinalis, Citrus limonum, Candida saitoana, Lens culinaria, Urtica dioica, Averrhoa carambola, Momordica charantia, Yarrowia lipolytica, Plumbago zeylanica* and so on.

Another ingredient that stimulates one or more of the above genes is a certain oligosaccharide obtained by controlled enzymatic depolymerization of membranous polysaccharides from brown seaweed such as *Laminaria digitata*. More specifically, the oligosaccharide is formed from urocanoic acids, in particular mannuronic acid and guluronic acids. Most preferred is an active having the INCI name "Hydrolyzed align" and having the CAS No. 73049-73-7.

The ingredient that stimulates that variably expressed gene may, in and of itself, also be a skin treatment active. Alternatively, the ingredient that stimulates the variably expressed gene may have only that efficacy, and if so, it is desirable to add one or more additional skin treatment actives. This will ensure that stimulating the variably expressed gene at a time when the gene is being maximally expressed in the majority of native untreated skin cells provides a treatment benefit. In particular, treatment benefits can be maximized in situations where the skin cells are acting synchronously. Prior to cellular synchronization, cellular biological pathways may not be running in exact synchronicity. However, even if this is the case, it can be said that normal circadian rhythms will cause most cells to be metabolically operating in the same general time frame.

Other Skin Actives

The treatment composition preferably contains one or more additional skin treatment actives. The skin treatment active may be anything that provides a benefit, such as skin whitening agents (via tyrosinase inhibition or other pathways), moisturizers, anti-acne agents, anti-inflammatory agents, anti-rosacea agents, cellular DNA repair actives, protein repair actives, anti-wrinkle agents, skin firming agents, blurring agents, oil absorbing actives, humectants, collagen or elastin stimulating actives, or specific ingredients that directly or indirectly contribute to providing the benefit. Such actives may be present in amounts ranging from about 0.00001 to 10%, preferably from 0.00005 to 5%, more preferably from about 0.0001 to 2%. Suitable benefit actives include, but are not limited to those set forth herein. Preferred are benefit actives that exhibit optimized efficacy when combined with the ingredient that stimulates the variably expressed gene.

DNA Repair Enzymes

The composition may contain one or more DNA repair enzymes. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base damage.

Another type of DNA repair enzyme that may be used is one that is known to be effective in repairing 06-methyl guanine base damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of various species of *micrococcus*), lecithin, and water. Photosomes® comprise a mixture of plankton extract (which is the extract of marine biomass which includes one or more of the following organisms: thalassoplankton, green micro-algae, diatoms, greenish-blue and nitrogen-fixing seaweed), water, and lecithin.

Other suitable DNA repair enzymes include Endonuclease V, which may be produced by the denV gene of the bacteriophage T4. Also suitable are T4 endonuclease; $O^6$-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase; $O^6$ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-5l; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The compositions of the invention may contain one or more DNA repair enzymes.

Proteasome Activators

The treatment composition may contain one more proteasome activators in amounts ranging from about 0.0001 to 65%, preferably from about 0.0005 to 50%, more preferably from about 0.001 to 40%. Suitable proteasome activators are any compounds, molecules, or active ingredients that stimulate proteasome activity in the cells of keratin surfaces. Proteasomes are protein complexes within cells that degrade damaged proteins. Ingredients that are proteasome activators will stimulate proteasome activity in cells where such activity may be reduced due to age, cellular damage such as what is caused by exposure to UV light.

Examples of suitable proteasome activators include, but are not limited to, algin, alginates, hydrolyzed algin, molasses extract, *Trametes* extracts, including extracts from *Trametes versicolor*, *Olea Europa* (Olive) fruit extract either alone or in combination with *Acacia senegal* extract, Pomiferin/Osajin, plankton extract, arginine ferulate, a composition comprising plankton extract/butylene glycol/arginine ferulate/water, yeast extract, Plankton extract, and a peptide referred to as UB5 (penta-ubiquitin).

Probiotic Microorganisms

The treatment composition may contain one or more probiotic microorganisms or lysates or filtrates thereof. The probiotic microorganism extract may be obtained from the fermentation of any probiotic bacteria or yeast including those from the order Lactobacillales or Bifidobacteriales, or the genus of yeast, *Saccharomyces*. More preferred bacteria are from Bifidobacteriales and Lactobacillales. Suitable bacteria from Lactobacillales order include the lactic acid producing bacteria from *Abiotrophia, Aerococcus, Camobacterium, Enterococcus, Lactobacillus, Lactococcus, Leuconostoc, Oenococcus, Pediococcus, Sporolactobacillus, Teragenococcus* genus and so on. Particularly desirable are bacteria from the *Lactobacillus* genus, of which there are a considerable number of species. Most preferred are *Lactobacillus Plantarum* or *Lactobacillus casei* or *rhamnosus*. P Suitable probiotics from Bifidobacteriales includes those from the *Bifidobacterium* genus. Particularly preferred are those from *Bifidobacterium longum* although other species may be suitable. Particularly preferred are inactivated bacterial lysates from *Bifidobacterium longum* which may be in the form of a fermentation product. Such ingredients have the INCI names Bifida lysate, Bifida ferment lysate, Bifida ferment filtrate. The *Bifidobacterium* may also be in the form of a mixture with other botanical extracts or ingredients, or in the form of a fermentation product.

Suitable probiotic yeasts include those from the genus *Saccharomyces*, including species such as *Saccharomyces cerevisiae. boulardii, bulderi*, and so on.

In one embodiment of the invention the *Bifidobacterium* is as set forth in U.S. Pat. No. 6,790,434 which is hereby incorporated by reference in its entirety.

In another embodiment of the invention the probiotic microorganism extract used in the color cosmetic composition is obtained as set forth in U.S. Pat. No. 7,510,734 which is hereby incorporated by reference in its entirety, and has the CTFA name *Lactobacillus* ferment, which is defined as an extract obtained from the fermentation of *Lactobacillus*. Commercial sources include those sold under the trade names AC Probiotic 1 by Active Concepts LLC or *Lactobacillus crispatus* KLB 46 sold by Natural F&P Co., Ltd of Korea. Also suitable are various derivatives including one having the CTFA name *Lactobacillus* Ferment Filtrate, which is a filtrate of the extract from *Lactobacillus* Ferment, which may be purchased from Active Concepts LLC as a mixture of salicylic acid and the filtrate sold under the trade name ACB Salicylic Acid Bioferment. Also suitable are derivatives having the CTFA names *Lactobacillus* Ferment Lysate which is a lysate of the extract from fermentation of *Lactobacillus*, or *Lactobacillus* Ferment Lysate Filtrate where the lysate of the extract from fermentation of *Lactobacillus* is filtered.

Also suitable are extracts from yeast such as *Saccharomyces* which are fermented alone or in combination with various plant materials, for example, apple, *ginseng*, garlic, and so on. Such ingredients have the CTFA names *Saccharomyces* Ferment, *Saccharomyces* Ferment Lysate, *Saccharomyces* Ferment Lysate Filtrate, *Saccharomyces*/grape ferment, *Saccharomyces/Lamanaria Saccharina* ferment, and so on; as well as extracts obtained from fermentation of *Saccharomyces* in combination with metals such as copper, calcium, magnesium, tourmaline, and so on.

Suitable ranges of the probiotic microorganism or ferment or lysate thereof may be from about 0.0001 to 35%, preferably from about 0.001 to 20%, more preferably from about 0.01 to 10%.

Other Ingredients

Other ingredients may be present in the treatment composition in order to provide a stable, cosmetically acceptable composition. Such ingredients include surfactants, thickening agents, preservatives, humectants, botanical extracts, other peptides or proteins, and the like.

More specifically, suitable surfactants particularly include nonionic organic or silicone based surfactants, preferably those having an HLB ranging from 5 to 13. More specifically, alkoxylated alcohols where the alkoxy group ranges from 1 to 26 carbon atoms, preferably fatty alkoxylated alcohols from lauric, stearic, behenic, or cetearyl alcohols. Examples include Laureth, Oleth, Gluceth, or methyl or ethyl derivatives thereof. More specific examples include PEG-75, methyl gluceth-20, Bis-PEG-18 methyl ether dimethyl silane, glycereth-26, PEG-8 glyceryl isostearate, oleth-3 phosphate, Laureth-3 and mixtures thereof. If present the surfactants may range from 0.01 to 10%.

Suitable thickening agents include aqueous or non-aqueous thickening agents such as carbomers, C10-30 alkyl acrylates crosspolymer, sodium polyacrylate, Polyacrylate crosspolymer-6, Polyacrylate crosspolymer-7 and so on. If present, such thickening agents may range from 0.1 to 10%.

Suitable humectants include alkylene glycols such as butylene, pentylene, propylene glycols, ethyl hexyl glycerin, glycerin and mixtures thereof. If present such humectants agents may range from 0.1 to 5%.

The composition may also contain one or more botanical ingredients such as *Porio cocos sclerotium* extract, *Silybum marianum, Anthemis nobilis, Magnolia officianalis* bark extract, *Garcinia mangostana* extract, *Cladosiphon okamaranus* extract, *Betula alba* extract, Artemia extract, and mixtures thereof. Such extracts may be present in amounts ranging from 0.001 to 5%, preferably from about 0.01 to 3%, more preferably from about 0.01 to 1%.

Suitable treatment compositions may contain:
50-95% water
0.001-5% botanical extracts
0.01-5% of the variable gene stimulating active,
0.01-5% of the skin treatment active,
0.01-5% of botanical extracts,
0.01-5% humectants; and
0.01-5% of a thickening agent.

Another suitable treatment composition may contain:
50-95% water,
0.01-5% of the variable gene stimulating active which is also a skin treatment active,
0.01-5% of a DNA repair enzyme; and
0.01-5% of inactivated bacterial lysates from *Bifidobacterium*.

The Methods

In the method of the invention the sheet pack is applied to the desired keratin surface for a period of time ranging from 1 to 60 minutes. However, one particular benefit of the sheet pack is that it provides effective skin treatment in 10 minutes or less. Most standard sheet pack products require 20-30 minutes. The amount of fill 24-25 ml. is perfect for treating a standard face having 20-40 square inches. The treatment composition remaining on the face after removal of the mask can be massaged into the skin as a treatment lotion or cream, and may obviate the need for applying additional moisturizers to the skin. Especially during periods of nightly rest, the skin barrier naturally becomes more permeable, thus permitting optimized treatment of skin. In one preferred embodiment the user instructions instruct the consumer to apply the sheet mask during the period of 12:00 to 24:00 hours, more preferably from 16:00-24:00, most preferably from 18:00 to 24:00 hours.

The invention also comprises a method for making a sheet pack comprising the steps of:

(a) identifying a gene that is variably expressed over a 24 hour period in native untreated skin cells, (b) forming a sheet pack comprised of an absorbent layer and, optionally, an impermeable layer bonded to the absorbent layer, (c) impregnating the absorbent layer with a treatment composition containing at least one ingredient that stimulates the gene in (a) above when topically applied to skin;

(d) packaging the sheet pack in a package containing user instructions to apply the sheet pack to the skin a time when the gene in (a) above is being maximally expressed in native untreated skin cells.

In step (a) the gene that is variably expressed over a 24 hour period in native untreated skin cells can be identified by the method set forth in Example 1, or similar methods.

Once the gene that is identified in (a) is determined, ingredients can be screened to determine their effect on gene expression in various types of cells such as skin cells. The ingredient that shows activity in stimulating the same gene identified in (a) above is selected. That ingredient is then formed into a treatment composition and impregnated into an absorbent layer as further described herein. A sheet pack is prepared by cutting the fabric into the desired shapes and packaging it into a package that contains user instructions to apply the sheet pack to the skin at time when the gene identified in (a) is being maximally expressed in native untreated skin cells.

The invention is also directed to a method for treating skin with a sheet pack comprising the steps of:

(a) forming a sheet pack comprised of absorbent layer and optionally bonded thereto an impermeable layer;

(b) impregnating the absorbent layer with a treatment composition containing at least one ingredient that stimulates a gene that is variably expressed over a 24 hour period in native skin cells when topically applied thereto, (c) topically applying the sheet pack to the skin at a time when same gene in (b) above is being maximally expressed in native untreated skin cells.

The method of the invention is as described herein. The invention will be further described in connection with the following examples which are set forth for the purposes of illustration only.

EXAMPLE 1

Figure 5:
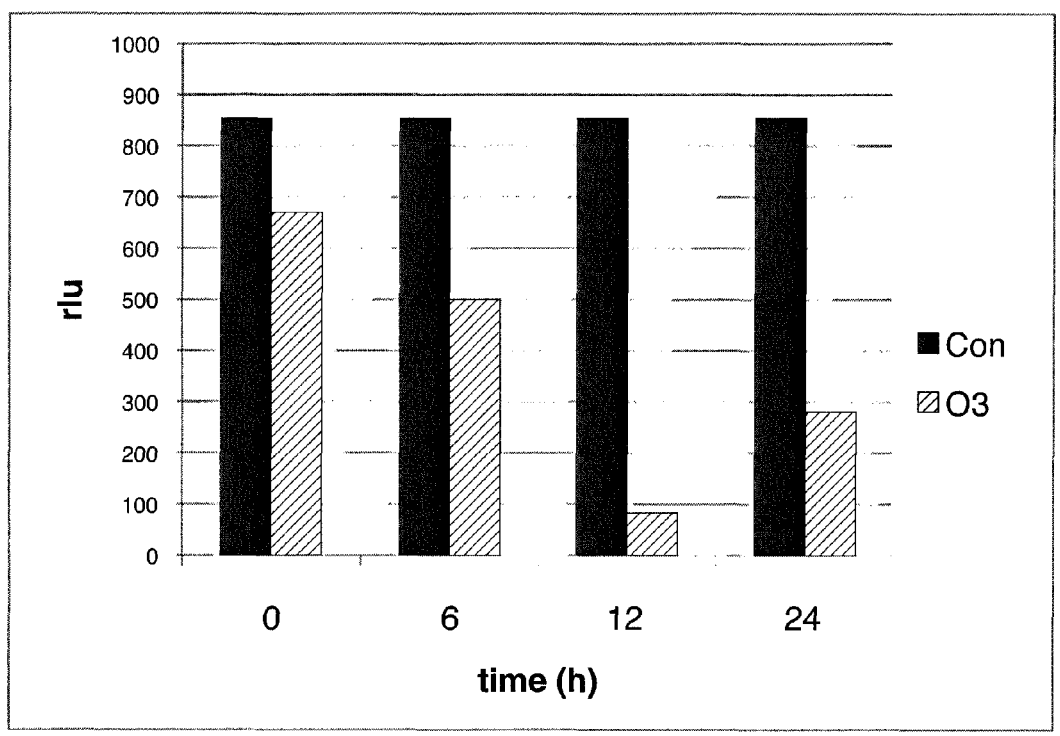
FIG. 5 depicts the results of testing untreated and ozone exposed cells to determine PER1 activity over a 24 hour period.

Per1 gene expression in normal human epidermal keratinocytes (NHEK) donors was tested in control cells and cells exposed to ozone using the reporter assay. NHEK were plated at a concentration of $3\times10^4$ in a black walled, 96 well microtiter plate for 3 hours in EpiLife media. The cells were then transfected in supplement free media with a plasmid that contained luciferase as the reporter gene ligated upstream to a per1 promoter element. In addition, transfection was facilitated by addition of Plus and Lipfectamine reagents (Invitrogen, Carlsbad, Calif.). Transfection in supplement free media was carried out for an additional four hours. This "starves" the cells which in turn causes them to be synchronized in their circadian rhythms. After transfection, full media neat and containing ozone was added and incubated for 16 hours. Then a luciferase reagent, Glo-Bright (Promega Corporation, Madison, Wis.) was added and luminescence measures in an Lmax luminometer (Molecular Devices, Sunnyvale, Calif.). The results are set forth in FIG. 5 and show that untreated cells show variable Per1 activity over a 24 hour period with the maximum activity occurring at time 0 (night) and slowly decreasing to its lowest level 12 hours later (day), and then increasing again at 24 hours. Ozone treated cells show a decrease in per1 activity at 0, 6, and 12 hours, with the cellular stabilization against the tox effects of ozone stabilizing by 24 hours. The results demonstrate the normal circadian rhythm of untreated cells as a function of per1 gene expression in NHEK.

Figure 6:
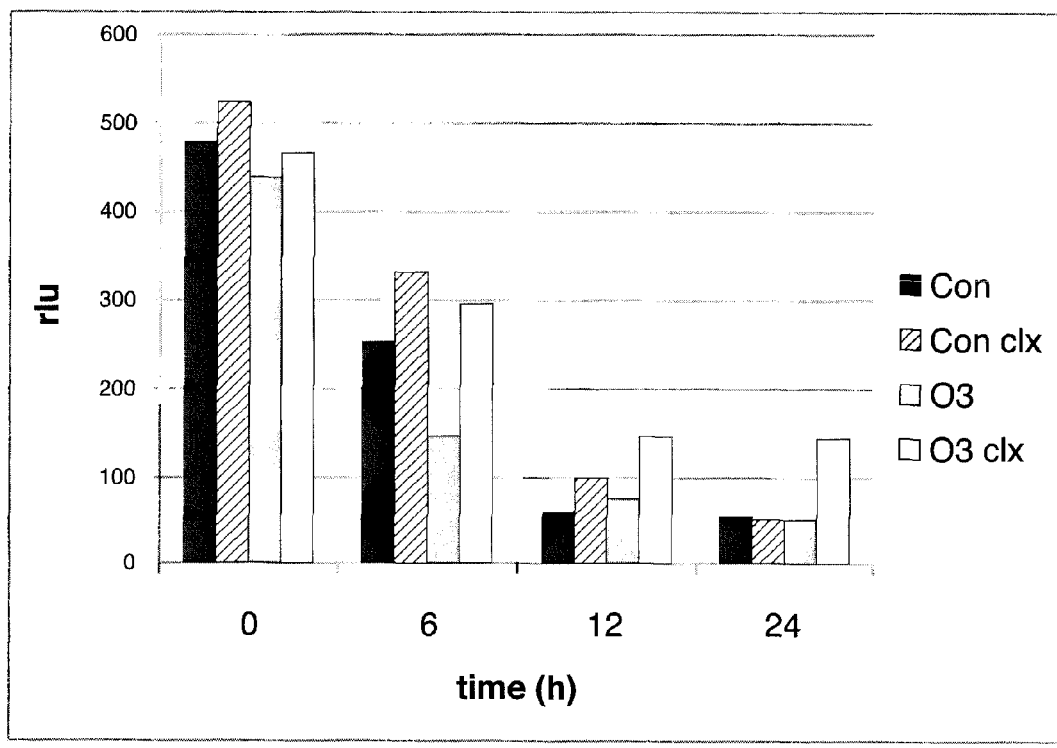
FIG. 6 depicts the results of testing time synchronized untreated cells, cells treated with Tripeptide-32 (a PER1 gene activator), cells treated with ozone, and cells treated with ozone and Tripeptide-32.

The test was performed again, and in addition, a peptide with per1 gene activity was tested. The results are set forth in FIG. 6. At 0 time synchronized untreated cells, cells treated with Tripeptide-32, cells treated with ozone, and cells treated with ozone and Tripeptide-32 clearly show that Tripeptide-32 is a per1 gene activator and increases per1 gene expression in untreated cells; and that this effect ameliorates the adverse effects found in cells treated with ozone. At 6 and 12 hours, the Tripeptide-32 treated cells with and without ozone show improved per1 gene expression when compared to untreated cells and cells treated with just ozone. At 24 hours the cells treated with ozone and Tripeptide-32 showed the highest level of per1 gene expression with the untreated cells, Tripeptide-32 treated cells, and ozone treated cells all showing lesser, and about equivalent, expression of PER1.

In both tests, NHEK were treated at the start of the test (0 hours) so that they were all synchronized with respect to their circadian rhythm, and expressing per1 at the same time. Over the 24 hour period, the level of per1 gene expression decreased to its lowest point at 12 hours, which corresponds to mid-day. The per1 activity then increased at 24 hours. However, since the cells synchronized at time 0 have not all maintained their synchronicity in tandem, but rather have begun to diverge in their circadian pathway, the increase in per1 gene expression is less than it was at 0 hours. The results show the natural circadian rhythm of cells over a 24 hour period and that expression of per1 increases at a time that is consistent in a 24 hour cycle; usually at night.

EXAMPLE 2

A treatment composition was prepared as follows:

| Ingredient | % by weight |
| --- | --- |
| Water | QS100 |
| Methyl gluceth-20 | 4.40 |
| PEG-75 | 4.00 |
| Bis-PEG-18 Methyl Ether Dimethyl Silane | 2.00 |

-continued

| Ingredient | % by weight |
| --- | --- |
| Butylene glycol | 1.40 |
| Propanediol | 1.10 |
| Glycereth-26 | 1.00 |
| PEG-8 Glyceryl Isostearate | 0.80 |
| Glycine | 0.50 |
| Squalane | 0.50 |
| Algae extract | 0.49 |
| Oleth-3 phosphate | 0.45 |
| Preservatives | 0.25 |
| Tocopherol acetate | 0.40 |
| Caffeine | 0.20 |
| Carbomer | 0.14 |
| Dextrin | 0.10 |
| Sodium hyaluronate | 0.07 |
| *Porio cocos Sclerotium* extract | 0.1 |
| Xanthan gum | 0.05 |
| Hydrolyzed rice extract | 0.03 |
| *Echinacea purpura* (Coneflower) extract | 0.03 |
| Laureth-3 | 0.03 |
| *Silybum marianum* (Lady thistle) extract | 0.02 |
| *Anthemis nobilis* (Chamomile) extract | 0.01 |
| Hydroxyethylcellulose | 0.01 |
| *Magnolia officinalis* bark extract | 0.01 |
| *Garcinia mangostana* peel extract | 0.01 |
| Yeast extract | 0.06 |
| Acetyl dipeptide-1 cetyl ester | 0.005 |
| *Cladosiphon okamuranus* extract | 0.005 |
| Glycerin | 0.005 |
| *Artemia* extract | 0.001 |
| *Betula alba* (birch) extract | 0.001 |
| Hydrolyzed algin | 0.0003 |
| *Lactobacillus* ferment | 0.0003 |
| Lecithin | 0.0003 |
| Ethylhexyl glycerin | 0.0002 |
| Coffee seed extract | 0.0001 |

The composition was prepared by combining the ingredients and mixing well.

EXAMPLE 3

Non-woven fabric comprised of 45-65% (55%) pulp, 25-45% (35%) rayon, and 5-15% (10%) polyester (Non-woven Fabric KP9650, Sansho Shigyo Co. Ltd, Tosa City, Kochi, Japan) was cut into a pattern for a face mask with holes for eyes, nose and mouth as depicted in FIG. 3. A second face mask was prepared by preparing a laminate of aluminum foil (Toyo Aluminum KK, Osaka Japan) comprised of aluminum and aluminum alloys (about 99.30% or more aluminum, 0.7% or less of each of Silicon and Iron, 0.1% of less of Copper, 0.05 or less of Manganese, 0.05% or less of Magnesium, and 0.05% or less of Zinc) with the same non-woven fabric. The non-woven fabric was loaded onto one spool. The aluminum foil onto a second spool. An extruder containing low density polyethylene (Petrothene, Tosoh Corporation, Tokyo Japan) extruded the resin between the two films which were compressed between a pressure bonding roller and a cooling roller as depicted in FIG. 2. A second sheet pack of the same design as in FIG. 2 was cut from the laminated film. The composition of Example 2 was impregnated into the non-woven layer of both sheet masks.

The masks were then tested for their efficacy in penetrating skin on skin models.

Fluorescein Skin Model Test

Migration of fluorescein through EFT-400 skin models into the media was measured using a fluorescent plate reader at specific time points (at t=0, 15 30 45, 60, 90, 120, 150, 180 min) and results were compared. A more penetrating effect attributed to the mask suggested more fluorescein migration into the media.

Materials:
EFT-400 Living Skin Equivalents: Mattek; EFT-400; Lot#17586; Kit E. ("LSE")
EFT 400 Media: Mattek; EFT-400-asy; Lot#092914GSA.
Fluorescein: Vendor: Sigma Cat# F6377-100G Lot#061M0048V
DPBS (Dulbecco's Phosphate Buffered Saline): Vendor: Corning Cellgro Cat#21-0341-CV Lot#21031456.

Masks Provided:
Face mask with absorbent layer only from non-woven fabric containing 55+/−5% pulp, 35+/−5% rayon, and 10%+/−5% polyester. Fabric purchased from Sansho Shigyo Co. Ltd.
Face mask with same absorbent layer as noted above, and in addition, an impermeable layer of metallic aluminum foil having a thickness of about 7 microns, purchased from Toyo KK, Osaka Japan. The two layers were bonded together as noted herein with low density polyethylene.
Dermal Biopsy Punch 8 mm (to cut pieces out of masks in 8 mm round circles to fit inside well of EFT-400)

Samples Tested: n=2
Blank—nothing applied to LSE (living skin equivalent)
25 ul DPBS only applied topically to LSE
25 ul Fluorescein @ 100 ppm diluted in DPBS applied topically to LSE
Absorbent layer only mask was layered over the LSE onto which 25 ul of Fluorescein @100 ppm was placed
Mask of laminate of absorbent layer and impermeable layer was layered over the LSE onto which 25 ul of Fluorescein @100 ppm was placed Procedure Assembled and fed 2.5 ml Media (EFT-400), and incubated overnight at standard conditions (5% $CO_2$/37° C./100% humidity). Maintained LSE's as per MatTek's EpiDerm Full Thickness 400 (EFT-400) Use Protocol.
1. Aspirated out existing Media and refreshed LSE's with 2.5 ml Media per well.
2. Using 8 mm biopsy punch small circles are cut neatly out of the provided samples as noted above
3. Pipetted 25 ul of DPBS on top of LSE on top of designated wells
4. Pipetted 25 ul of Fluorescein in DPBS only (100 ppm) on top of LSE
5. Placed the die-cut absorbent layer only circle into the LSE well and pipetted 25 ul of 100 ppm Fluorescein in DPBS onto the fabric of the mask; also with wells containing DPBS only control
6. Picked up die-cut laminate of absorbent layer and impermeable layer. While holding the circle over the well, saturated the absorbent layer with 25 ul of 100 ppm Fluorescein in DPBS. Then quickly apply die-cut mask piece soaked disk with soaked side down into EFT well.
7. Supernatant was drawn out of the bottom well of the LSE at various time-points as indicated below and read using fluorescent analysis via plate-reader following final read (t=3 hr).
   i. Settings used were: Bottom Read Ex: 494 em: 521 Cutoff 515

Collected 250 ul of supernatant at the following time-points and stored in 0.5 ul micro-centrifuge tubes (store protected from light, at 4° C.) for fluorescent plate-read following 3 hour time-point in minutes: 0, 15, 30, 45, 60, 90, 120, 150, and 180.

A standard curve was created using a serial dilution of 100 ppm Fluorescein diluted in EFT-400-ASY Media and pipetting 100 ul of each dilution into the wells of a 96-well plate as per the template below. Two plates were prepared: one for the standard curve measurements and one for the test samples. Preparing Standard Curve Samples (n=2):

Utilizing eight 1.5 ul Eppendorf tubes a serial dilution set was created:

Pipette 1,000 ul of 100 ppm Fluorescein in Media EFT-400media in tube#1

In tubes 2-8 add in 500 ul of EFT-400-ASY Media only

Starting with tube#1 transfer 500 ul of 100 ppm Fluorescein from tube 1 into tube 2 and pipette up and down to mix thoroughly to create a final concentration in Tube#2 of 50 ppm.

Figure 7:
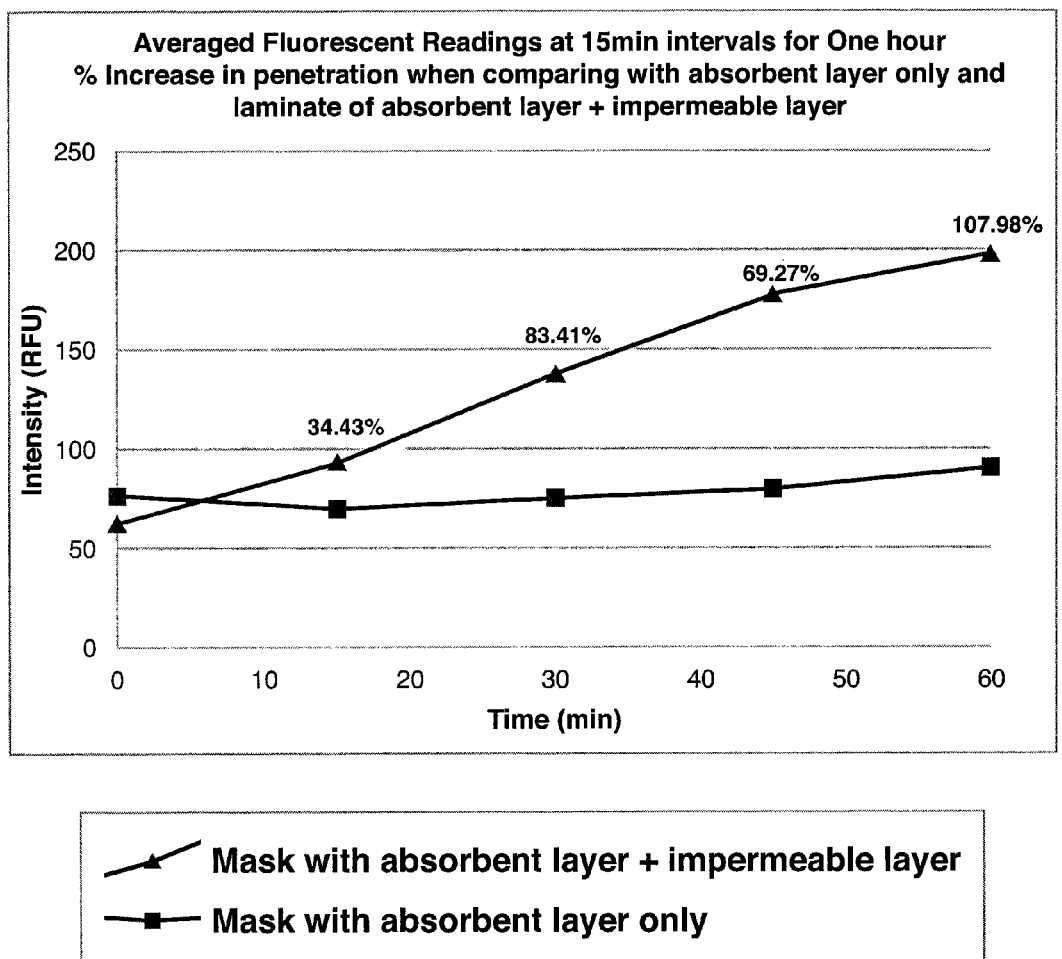
FIG. 7 depicts the results of penetration studies showing that when the treatment composition is impregnated into the laminate sheet mask of the invention the treatment composition shows significantly improved (up to 25%) penetration into skin when compared to the same sheet mask containing only an absorbent layer and no impermeable layer.

Then, after thoroughly mixed, pipette 500 ul from tube #2 and deliver into tube#3, pipette up and down to mix thoroughly. Creating a final concentration in Tube#3 of 25 ppm Continue this serial transfer for remaining tubes, each series dilution reducing the concentration in the following tubes by half Pipette 100 ul of solution per well from each tube to the corresponding wells of the 96 well plate A second plate with each sample at each time-point is created and read right after the standard curve 100 ul n=1.
Hour-Sample
A=nothing in well
B=nothing in well
C=25 ul DPBS only
D=25 ul DPBS only well
E=25 ul 100 ppm Fluorescein in DPBS well
F=25 ul 100 ppm Fluorescein in DPBS well
G=25 ul 100 ppm Fluorescein on absorbent layer only well
H=25 ul 100 ppm Fluorescein on absorbent layer only well
I=25 ul 100 ppm Fluorescein on full mask well
J=25 ul 100 ppm Fluorescein on full mask well The results were calculated and are graphically demonstrated in FIG. 7. The sheet mask comprised of a laminate of a metallic foil layer bonded to an absorbent layer showed consistently improved skin penetration when compared to the mask comprised only of the non-woven layer absorbent layer. Skin penetration means that the ingredients present in the composition were actually absorbed into the skin. While an impermeable layer may or may not cause less evaporation of the treatment composition from the skin during the period of use, this does not necessarily correlate with penetration. For example, the treatment composition could simply remain superficially on the skin surface.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

---

The invention claimed is:

1. A sheet pack in the form of a laminate having a thickness of 0.2 to 1.5 mm comprising a skin penetration enhancing impermeable layer comprised of metallic foil having a thickness ranging from 2 to 15 microns permanently fused to an absorbent layer comprised of cotton pulp with a heat activated bonding agent which is a thermoplastic material having a melting point ranging from 200 to 300° C. where the absorbent layer is impregnated with an aqueous based a treatment composition having a viscosity of 2 to 1,000 centipoise at 25° C. and a specific gravity of 1.0 to 1.010, containing an ingredient selected from the group consisting of (a) a CLOCK gene activator, (b) a PER gene activator, (c) a BMAL gene activator, (d) a CRY gene activator, or (e) combinations thereof; the sheet pack contained in a package with user instructions to topically apply the absorbent layer side of the sheet pack laminate for a period of 1 to 60 minutes to the skin at a select time period ranging from 1800 to 2400 hours wherein the skin penetration of the treatment composition is improved compared to a sheet pack containing the same absorbent layer but having no impermeable layer permanently fused to the absorbent layer.

2. The sheet pack of claim 1 wherein the treatment composition comprises a CLOCK gene activator.

3. The sheet pack of claim 1 wherein the bonding agent is a low density polyethylene.

4. The sheet pack of claim 3 wherein the absorbent layer is in the form of a non-woven fabric.

5. The sheet pack of claim 4 wherein the absorbent layer is a non-woven fabric having one or more of the following specifications:
   (a) absorbs water from 0.03 to 2.5 ml/gram after 5 seconds per 1 gram measured by the Larose method,
   (b) a thickness ranging from 0.1 to 1.0 mm,
   (c) a bending resistance of 1.0 to 2.0 mm·m$^2$/gram,
   (d) a drape co-efficient ranging from 1 to 70%,
   (e) a KES bending rigidity B value of less than or equal to 0.20 gf/cm$^2$/cm; or
   (f) a co-efficient of friction of less than 0.45 MIU.

6. The sheet pack of claim 5 wherein the non-woven fabric comprises a mixture of cotton, rayon, and synthetic fibers.

7. The sheet pack of claim 6 wherein the non-woven fabric comprises 25-75% pulp (cotton), 10-50% rayon, and 2-15% polyester.

8. The sheet pack of claim 5 wherein the impermeable layer is a metallic foil having of the following specifications:
   (a) from about 98 to 100% aluminum,
   (b) a melting point of greater than 650° C.
   (c) a specific gravity of 2.5 to 3.0,
   (d) a thickness ranging from 2 to 15 microns.

9. The sheet pack of claim 4 wherein the absorbent layer is bonded to the impermeable layer by a heat activated bonding agent that is a synthetic polymer having melting point ranging from 221 to 248° C. and a specific gravity of 915 to 935 kg/m$^3$.

10. The sheet pack of claim 1 wherein the impermeable layer causes the treatment composition to show at least a 10% improvement in skin penetration of the treatment composition into the skin when compared to the skin penetration of the treatment composition with a sheet pack containing the same absorbent layer but with no impermeable layer being bonded to the absorbent layer.

11. The sheet pack of claim 4 wherein the absorbent layer is bonded to the impermeable layer by a heat activated bonding agent which is low density polyethylene having a specific gravity of 915 to 935 kg/m$^3$.

12. The sheet pack of claim 1 wherein the skin treatment composition comprises a PER gene activator.

13. The sheet pack of claim 1 wherein the skin treatment composition comprises a BMAL or CRY gene activator.

14. The sheet pack of claim 1 where the activator of CLOCK, PER, CRY, or BMAL is one or more of:
   Cichoric acid,
   *Echinacea* extract,
   Tripeptide-32,
   Tetrapeptide-26; or
   an Autophagy activator.

15. The sheet pack of claim 1 containing an additional skin treatment active selected from the group consisting of: a DNA repair enzyme, a probiotic microorganism, a proteasome activator, or combinations thereof.

16. The sheet pack of claim 1 for treating facial or body skin.

17. The sheet pack of claim 1 wherein the user instructions are to apply the sheet pack to the skin for about 10 minutes.

18. The sheet pack of claim 15 wherein the user instructions are to apply the sheet pack to the skin for a time ranging from 1 to 30 minutes.

19. The sheet pack of claim 15 wherein the user instructions are to massage the excess treatment composition into the skin after removal of the sheet pack from the skin.

20. The sheet pack of claim 1 where the activator of CLOCK, PER, CRY, or BMAL is a peptide.

* * * * *

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
      or no amino acid
<220> FEATURE:
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
```

1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)
<223> OTHER INFORMATION: Xaa can be cysteine or methionine or no amino
      acid
<220> FEATURE:
<221> NAME/KEY: misc_feature
<222> LOCATION: (2)
<223> OTHER INFORMATION: Xaa can be serine or threonine or no amino acid
<220> FEATURE:
<221> NAME/KEY: misc_feature
<222> LOCATION: (7)
<223> OTHER INFORMATION: Xaa can be alanine, glycine, isoleucine,
      leucine, proline, valine or no amino acid
<220> FEATURE:
<221> NAME/KEY: misc_feature
<222> LOCATION: (8)
<223> OTHER INFORMATION: Xaa can be asparagine, glutamine or no amino

```
       acid

<400> SEQUENCE: 7

Xaa Xaa Ser Pro Leu Gln Xaa Xaa
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Ser Pro Leu Gln
1
```